United States Patent [19]

Burns et al.

[11] 4,449,529

[45] May 22, 1984

[54] AUTOMATIC RETRACTABLE LANCET ASSEMBLY

[75] Inventors: James A. Burns, Elizabeth; Edward L. Nugent, N. Caldwell, both of N.J.

[73] Assignee: Becton Dickinson and Company, Paramus, N.J.

[21] Appl. No.: 322,345

[22] Filed: Nov. 18, 1981

[51] Int. Cl.³ ............................................. A61B 17/34
[52] U.S. Cl. ................................. 128/314; 128/329 R; 128/637
[58] Field of Search .................. 128/314, 315, 329 R, 128/770, 330, 637; 604/136, 137, 157

[56] References Cited

U.S. PATENT DOCUMENTS

| 55,620 | 6/1866 | Capewell | 128/329 R |
|---|---|---|---|
| 1,135,465 | 4/1915 | Pollock | 128/314 |
| 3,030,959 | 4/1962 | Grunert | 128/329 R |
| 4,120,303 | 10/1978 | Villa-Massone et al. | 128/330 |
| 4,139,011 | 2/1979 | Benoit et al. | 128/329 R |
| 4,185,635 | 1/1980 | Burford et al. | 128/330 |
| 4,203,446 | 5/1980 | Hofert et al. | 128/329 R |
| 4,230,118 | 10/1980 | Holman et al. | 128/314 |
| 4,388,925 | 6/1983 | Burns | 128/314 |

FOREIGN PATENT DOCUMENTS

| 124247 | 3/1949 | Sweden | 128/329 R |

*Primary Examiner*—Michael H. Thaler
*Attorney, Agent, or Firm*—Robert P. Grindle

[57] ABSTRACT

An automatic retractable lancet assembly includes a housing with a sharp-pointed lancet movably mounted therein. A slidable plunger is mounted in the housing in the end thereof opposite from the lancet for loading the assembly prior to use. An actuating mechanism releases the lancet for outward movement from the housing. After this outward movement is completed, the actuator elements become dissociated from further movement of the lancet. Subsequently, the lancet is automatically retracted back inside the housing by virtue of a spring element.

13 Claims, 11 Drawing Figures

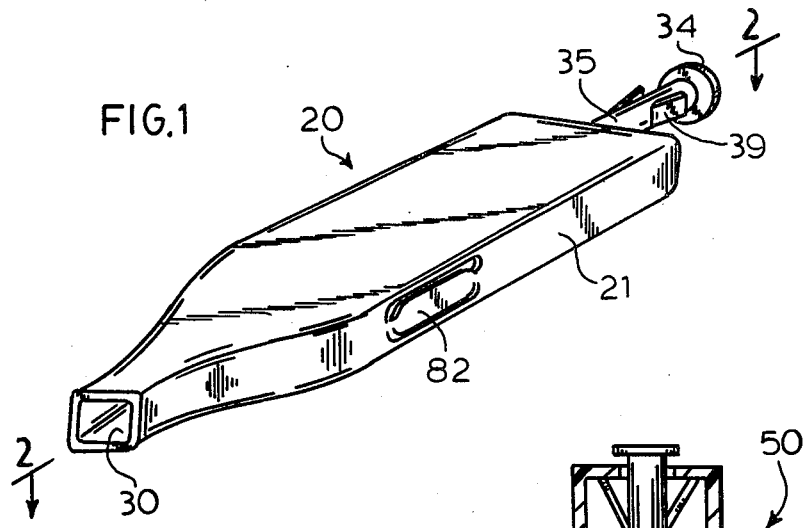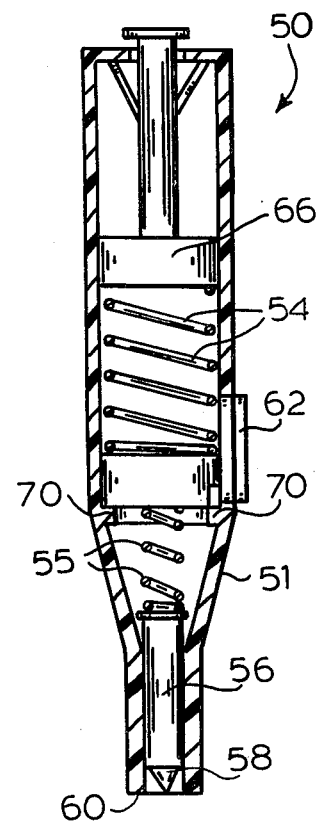

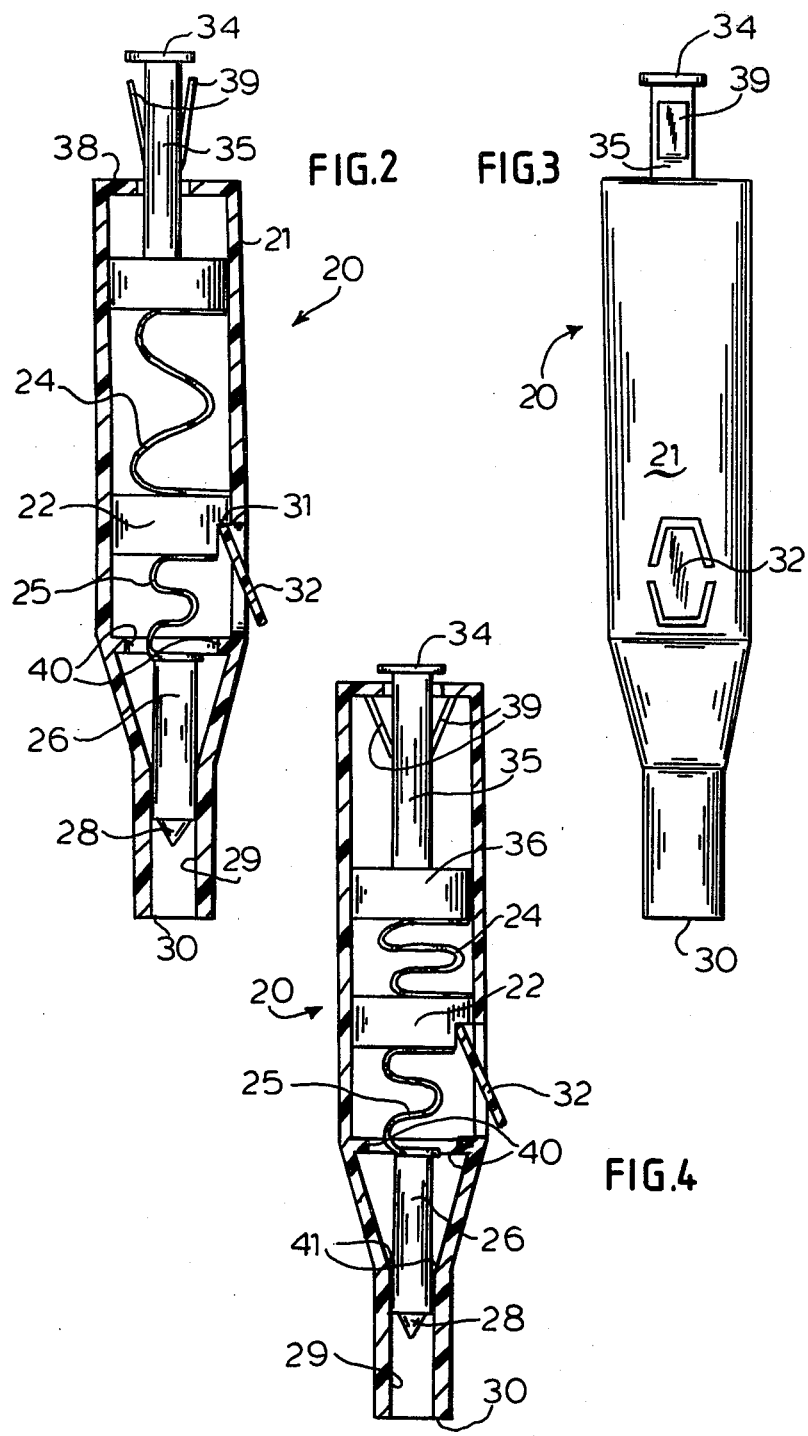

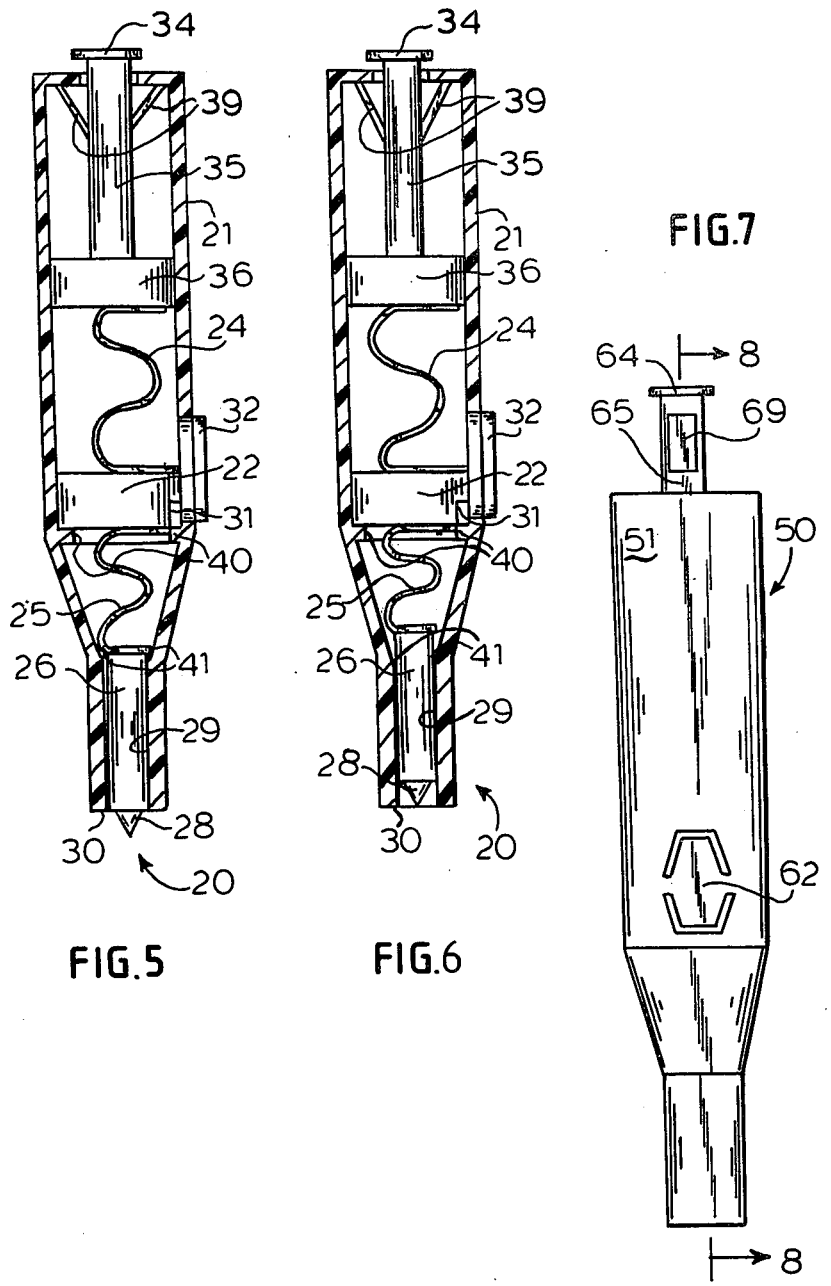

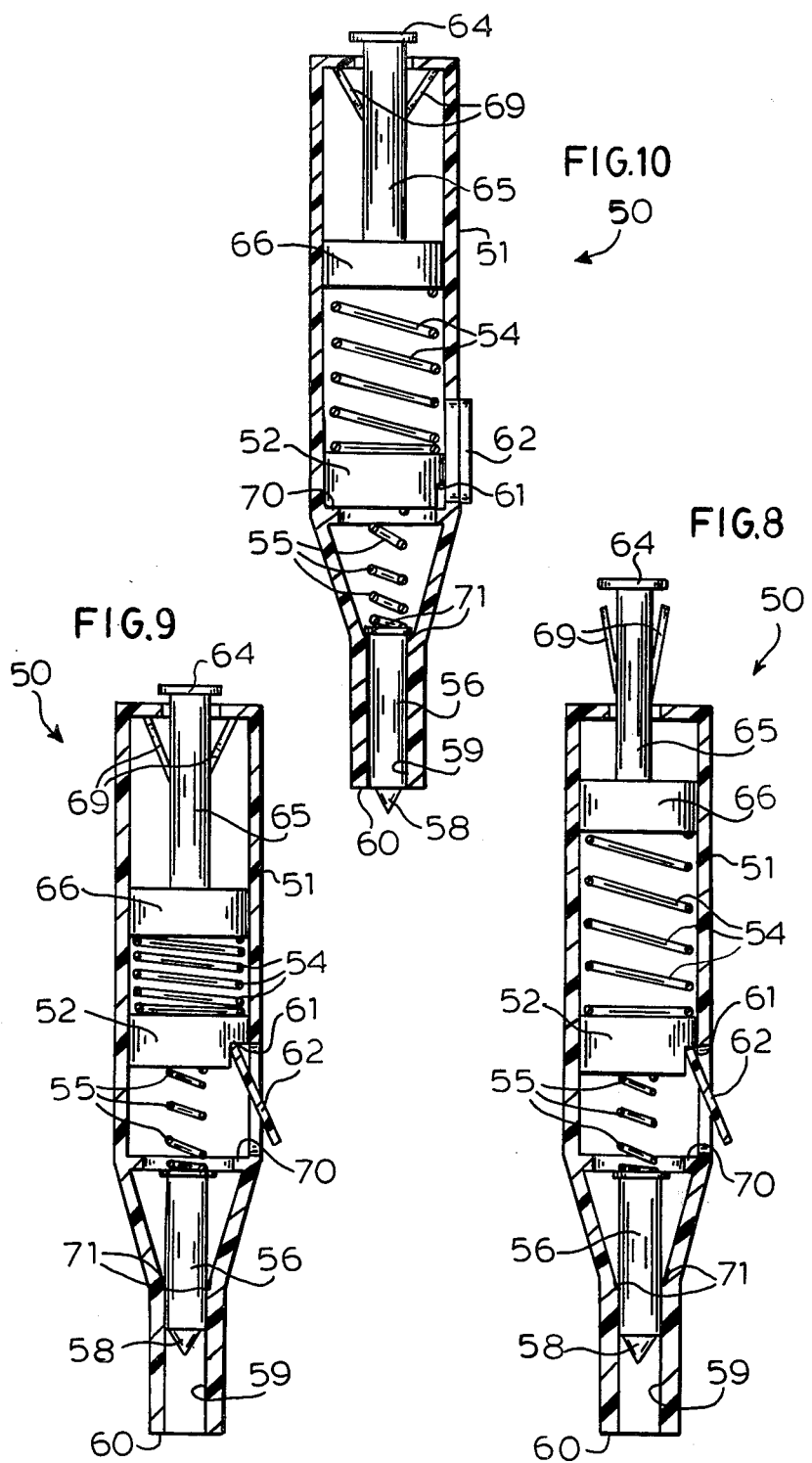

AUTOMATIC RETRACTABLE LANCET ASSEMBLY

BACKGROUND OF THE INVENTION

1. Field of the Invention

The present invention relates to a lancet assembly, and more particularly, concerns an automatic retractable lancet assembly useful in penetrating the skin of a patient.

2. Description of the Prior Art

Sharp-pointed lancets are employed to make a quick puncture or penetration of the patient's skin in order to provide a small outflow of blood. Various tests may be employed with only small amounts of blood so that the blood flowing from a finger prick is normally sufficient. However, due to the sensitive nerve endings in the finger tip area, this procedure could induce a significant amount of pain in the patient even though the skin puncture produces minimal cutting. In order to minimize potential pain, it is desirable to make the thrust of the lancet through the patient's skin rapidly.

Spring-loaded lancets of different types and forms have been well known and are typified, for example, by U.S. Pat. Nos. 55,620; 1,135,465; 3,030,959; 4,139,011; 4,203,446; 4,230,118; Swedish Pat. No. 124247 and Sutor, A. H., et al., "Bleeding From Standardized Skin Punctures: Automated Technique for Recording Time, Intensity and Pattern of Bleeding," A. J. C. P., Volume 55, May 1971. An improvement in a spring-loaded lancet is also described in an application entitled "Automatic Retractable Lancet Assembly," assigned in common with the assignee of the present application and filed in the U.S. Patent and Trademark Office on an even date herewith.

U.S. Pat. No. 4,203,446, above, is significant in that it teaches the puncture of the skin of a patient with a lancet which is retracted back into the device after piercing the patient's skin. In the patented device, the downward motion of the lancet is initiated by the impact of a spring-loaded hammer, and as this motion continues the spring potential decreases. At the time of impact, the return spring begins to compress and increase potential energy. When the potential energy in the return spring under compression exceeds the potential energy in the driving spring, compression of the return spring ends and decompression begins. This, then, reverses the motion of the lancet. However, impact is necessary to compress the return spring and increase its potential energy rapidly. Without the impact force, the spring forces would approach equilibrium and then there would be no reverse motion in order to retract the lancet out of the patient's skin. Furthermore, since spring potential is critical in this patented device, a conical spring is relied upon to overcome recoil due to the surge of the larger return spring. Despite the foregoing inventions, improvements in this field of lancets are still being sought.

SUMMARY OF THE INVENTION

An automatic retractable lancet assembly of the present invention comprises a housing having an aperture. A lancet is movably mounted in the housing with its point lying substantially adjacent the interior side of the aperture. A first spring is mounted inside the housing in a substantially relaxed condition. This spring is adapted to be compressed in a biased condition and is further adapted to decompress upon its release to cause the movement of said lancet outward of said aperture for penetration of the skin of a patient. The first spring is adapted to become dissociated from further movement of the lancet after the lancet completes its outward movement. Actuating means is provided for compressing the first spring into a biased condition and for retaining same until use, and for releasing same to cause the outward movement of the lancet. Included in the actuating means is spring compressing means movably mounted in the housing in the end thereof opposite from said lancet. A second spring is mounted inside the housing in a substantially relaxed condition before the first spring is released. This second spring is adapted to become biased when the first spring becomes dissociated from further movement of the lancet to cause the lancet to be automatically retracted back inside the housing.

In the preferred embodiment of the present invention, the second spring is mounted in the housing so that it is adapted to stretch to thereby become momentarily biased when the first spring becomes dissociated from further movement of the lancet. In this embodiment, the first spring is preferably a flat coil spring having a plurality of compressible folds lying substantially along a flat plane inside the housing. Similarly, the second spring is a flat coil spring having a plurality of compressible folds lying substantially along the same flat plane in the housing as the first spring. So that the first spring will be stronger than the second spring, the second spring generally has fewer folds than the first spring.

In another preferred embodiment of the present invention, the first and second springs are coiled helical springs serving the same functions as the previously described embodiment.

In accordance with the principles of the present invention, the desired functions are achieved by virtue of structure which is notably different from the structure of prior art lancet assemblies. In particular, and in the preferable embodiment, two springs are employed to complete the intended purpose of the lancet. The first spring serves as a driving spring to rapidly thrust the lancet outwardly for penetration of the patient's skin. At this time, this driving spring becomes dissociated from movement of the lancet. The second spring serves as a return spring, operable after the driving spring has become so dissociated. Therefore, when the second or return spring automatically retracts the lancet back into the housing, there is no opposing spring force, such as found in U.S. Pat. No. 4,203,446. Thus, in the present invention, the various spring potential energies do not have to balance as in the aforementioned patented invention. The return spring of the present invention only has to be sufficiently strong to retract the lancet inwardly. Therefore, considerations of balancing spring forces, as in the previous inventions, have been obviated by the structure of the present invention. This allows the design of the present invention to include a greater liberality as far as spring sizes and strengths are concerned. Advantageously, the present invention provides a quick thrust of the lancet outwardly to penetrate the skin of the patient, and then automatically retracts the lancet from the patient's skin so that dwell time therein is minimized. It is intended that this embodiment of the present invention can be economically fabricated so that it can be discarded after single use in disposable fashion.

BRIEF DESCRIPTION OF THE DRAWINGS

FIG. 1 is a perspective view illustrating the preferred embodiment of the automatic retractable lancet assembly of the present invention;

FIG. 2 is a cross-sectional view taken along line 2—2 of FIG. 1 illustrating the assembly as it may appear before use;

FIG. 3 is a side view of the lancet assembly of FIG. 1;

FIG. 4 is a cross-sectional view of the lancet assembly of FIG. 1 illustrated in the loaded condition for use;

FIG. 5 is a cross-sectional view of the lancet assembly of FIG. 10 illustrating the assembly after it has been fired with the lancet point in position to penetrate the skin of a patient;

FIG. 6 is a cross-sectional view of the lancet assembly of FIG. 10 illustrating the lancet retracted back inside the assembly after use;

FIG. 7 is a side view of an alternate embodiment of the lancet assembly of the present invention;

FIG. 8 is a cross-sectional view taken along line 8—8 of FIG. 7 illustrating the assembly in a pre-loaded condition;

FIG. 9 is a cross-sectional view of the lancet assembly of FIG. 7 illustrated in the loaded condition for use;

FIG. 10 is a cross-sectional view of the lancet assembly of FIG. 7 illustrating the assembly after it has been fired with the lancet point in position to penetrate the skin of a patient; and FIG. 11 is a cross-sectional view of the lancet assembly of FIG. 7 illustrating the lancet retracted back inside the assembly after use.

DETAILED DESCRIPTION

While this invention is satisfied by embodiments in many different forms, there is shown in the drawings and will herein be described in detail preferred embodiments of the invention, with the understanding that the present disclosure is to be considered as exemplary of the principles of the invention and is not intended to limit the invention to the embodiments illustrated. The scope of the invention will be measured by the appended claims and their equivalents.

Adverting to the drawings and FIGS. 1-3 in particular, lancet assembly 20 is comprised of a relatively flat housing 21 which may be fabricated in two parts for ready assembly. Inside housing 21 is a first block 22 to which two springs are connected: a first preferably flat coil spring 24 and a second also preferably flat coil spring 25. Both of the coil springs preferably have a plurality of compressible folds lying substantially along a flat plane inside housing 21, although spring 24 preferably has a higher spring constant than spring 25. Connected to the other end of flat spring 25 is a lancet block 26. At the distal end of lancet block 26 is a sharp pointed lancet 28. It is preferred that springs 24 and 25, block 22 and lancet block 26 be fabricated as an integral, unitary structure. For example, and while other materials may be used, the composite structure of springs, and two blocks, may be made of plastic material with the flat springs being very thin and thus highly resilient in nature. Lancet 28 at the distal end of lancet block 26 is preferably made of metal to facilitate penetration of the skin of a patient.

FIG. 2 depicts lancet assembly 20 in a relaxed, or preloaded condition. In FIG. 2, there is no compression on either of the springs. Lancet block 26 is partially positioned in bore 29 at the distal end of housing 21. Bore 29 terminates in an aperture 30 at the distal end of the housing. Block 22 is adapted to slide inside the interior of housing 21 and is dimensioned accordingly. Block 22 includes a notch 31 partially cut from its body so that a depressible button 32 may be engaged therein. Button 32 is preferably a cut-out portion of housing 21 adapted to pivot, for example, on a living hinge (not shown) formed in housing 21.

Turning now to FIG. 4, lancet assembly 20 is loaded by pressing inwardly on flange 34 at the top of a slidable plunger 35. Connected to plunger 35 inside housing is a slidable piston 36. It can be seen in FIG. 4 that when plunger 35 is depressed inwardly, piston 36 compresses spring 24. Block 22 remains stationary due to the fact that depressible button 32 is engaged in slot 31. Plunger 35 is depressed through opening 38 in the top of the housing so that the pair of resilient arms 39 also passes through opening 38. Once the arms are inside the interior of the housing, their resilient nature causes them to resiliently deflect outwardly beyond the diameter of opening 38. This latching arrangement effectively prevents plunger 35 from moving back out of housing 21. Therefore, once plunger 35 is depressed to load the lancet assembly, it cannot be readily reloaded, thereby preventing inadvertent reuse. This feature contributes to the disposable nature of the lancet assembly being discussed.

In the loaded condition for firing, spring 24 is under compression, whereas spring 25 remains in the relaxed condition. Referring now to FIG. 5, depressible button 32 is pushed at its lower end (as indicated by the arrow) so that the button becomes disengaged from slot 31 in block 22. This immediately releases the compression on spring 24 and causes block 22 to move distally in the direction toward aperture 30. However, a pair of abutment stops 40 inside housing 21 limits the travel of block 22 after the tension in spring 24 has been released. When block 22 strikes stops 40, the linear momentum of lancet block 26 causes spring 25 to stretch and become biased due to its resilient nature. When this occurs, lancet block 26 slides through bore 29 until lancet 28 emerges outward of aperture 30. A shoulder 41 inside the housing also limits the travel of the lancet block through bore 29 so that the emergence of lancet 28 can be controlled. Penetration of the skin of a patient would occur at this step of the utilization of lancet assembly 20.

The occurrence depicted in FIG. 5, it is understood, is only momentary due to the characteristics of spring 25. As illustrated in FIG. 6, spring 25 has returned to its normal relaxed condition, at the same time retracting lancet block 26, with lancet 28, back inside housing 21. It is understood that the retraction mechanism of spring 25 is independent of any action of spring 24. This is due to the fact that once spring 24 is completely or partially relaxed after being compressed, it is no longer associated with movement of lancet 28. Therefore, when spring 25 returns back to its relaxed condition it is not balancing any spring force remaining in spring 24, but is merely acting independently. The action of spring 25 to return to its relaxed condition, therefore, automatically retracts the lancet back inside the housing. The entire sequence to release the lancet and retract same occurs very quickly so as to minimize trauma to the patient. It can be seen by referring to FIG. 6, that once the lancet is retracted back inside the housing, the assembly cannot be reused and is therefore ready to be disposed.

Another embodiment of a lancet assembly employing the principles of the present invention is illustrated in FIGS. 7-11. Essentially, lancet assembly 50 is the same as lancet assembly 20, except that housing 51 is substantially cylindrically shaped, rather than generally flat as in the previous embodiment. Also, instead of flat coil springs as in the previous embodiment, lancet assembly 50 includes a first coiled helical spring 54 situated between piston 66 and block 52, and a second coiled helical spring 55 situated between block 52 and lancet block 56. Coiled helical spring 54 is selected to have a greater spring constant than coiled spring 55, so as to be stronger in nature.

Lancet assembly 50 is shown in the loaded condition in FIG. 9, which is similar to the loaded condition of the previous embodiment of FIG. 4. Slidable plunger 65 has been pressed inwardly on flange 64 so that piston 66 compresses coiled helical spring 54 against block 52. Block 52 remains stationary due to the fact that depressible button 62 is engaged in slot 61 partially cut from the body of block 52. At this time, second coiled helical spring 55 remains in the relaxed condition.

Referring now to FIG. 10, depressible button 62 is pushed at its lower end so that it becomes disengaged from slot 61. This immediately releases the compression on spring 54 and causes block 52 to move distally in the direction toward aperture 60. A pair of abutment stops 70 inside housing 51 limits the travel of block 52 after the tension in spring 54 has been released. At this time, spring 55 stretches and becomes biased; when this occurs, lancet block 56 slides through bore 59 until lancet 58 emerges out of aperture 60. Penetration of the skin of a patient would occur at this step.

After momentary emergency of lancet 58, spring 55 returns to its normal relaxed condition, at the same time retracting lancet block 56, with lancet 58, back inside housing 51. It is understood that the retraction mechanism of spring 55 is independent of any action of spring 54. This is due to the fact that once spring 54 is completely or partially relaxed after being compressed, it is no longer associated with movement of lancet 58. Therefore, when spring 55 returns back to its relaxed condition, it is not balancing any spring force remaining in spring 54, but is merely acting independently.

Thus, there has been provided in accordance with the present invention an automatic retractable lancet assembly. While two springs are preferably employed, the return spring operates independently and is dissociated from any movement of the driving spring. Accordingly, balance of spring forces is not required as in prior art lancet assemblies. This allows more straightforward operation, reduction of spring sizes and lighter weight materials.

What is claimed is:

1. A throw-away single use automatically retractable lancet assembly, comprising
   (a) a housing:
   (b) an aperture positioned in one end of said housing;
   (c) a lancet in said housing adjacent said aperture, said lancet mounted for reciprocable movement through said aperture;
   the improvement characterized by
   (d) lancet actuating means mounted in said housing in the end thereof opposite said aperture;
   (e) a first spring mounted in said housing and positioned between said lancet actuating means and said lancet;
   (f) said first spring being movable from a first compressed position to a second relaxed position upon release to cause movement of said lancet outward through said aperture for penetration of the skin of a patient;
   (g) means for dissociating said first spring in said second position from further movement of said lancet;
   (h) said lancet actuating means movable through said housing end from a first non-charge position to a second charge position for moving said first spring from a relaxed state to a compressed state;
   (i) release means in said housing for retaining said first spring in said first position and for the release of said first spring to cause the said movement thereof from said first-position to said second position for causing outward movement of said lancet through said aperture;
   (j) a second spring positioned between and connecting said first spring and said lancet;
   (k) said second spring being movable from a first relaxed position maintained at both the non-charged and charged position of said actuating means with said lancet withdrawn from said aperture;
   (l) to a momentarily extended condition momentarily thrusting said lancet through said aperture back to a relaxed position with the lancet withdrawn from the aperture.

2. The assembly of claim 1 wherein said second spring means is mounted in said housing so that it is adapted to stretch during the said momentarily extended position thereof to thereby become momentarily biased when said first spring becomes dissociated from further movement of said lancet.

3. The assembly of claim 1 wherein said first spring is a flat coil spring having a plurality of compressible folds lying substantially along a flat plane inside said housing.

4. The assembly of claim 3 wherein said second spring is a flat coil spring having a plurality of compressible folds lying substantially along the same flat plane in said housing as said first spring.

5. The assembly of claim 4 wherein a slidable block is positioned inside said housing with the interior ends of said respective springs being connected to said block, said block adapted to slide in the direction toward said aperture but not in the direction opposite said aperture when said first spring moves from said first position to said second position.

6. The assembly of claim 5 wherein said housing further includes an abutment stop for engaging said block after said first spring becomes decompressed to limit the sliding movement of said block and to enhance the movement of said second spring to said momentarily extended position.

7. The assembly of claim 6 wherein the other end of said second spring engages a lancet block slidably mounted in said housing, said lancet being mounted at the distal end of said lancet block for movement through said aperture.

8. The assembly of claim 4 wherein said first and second springs, said block and said lancet block are formed of plastic material.

9. The assembly of claim 8 wherein said first and second springs, said block and said lancet block are formed as an integral, unitary structure.

10. The assembly of claim 1 wherein said second spring is a coiled helical spring.

11. The apparatus of claim 1, further characterized by
(a) said lancet actuating means including a plunger reciprocable through said one end of said housing from a first position maintaining said first spring in a relaxed position to a second position compressing said first spring to its said first compressed position; and
(b) cooperating latching means on said plunger and said housing to maintain said first spring in its first compressed position.

12. The assembly of claim 11 wherein said latching means includes at least one resilient arm adapted to slide with said plunger into said housing and, once inside said housing, resiliently flex away from said plunger to prevent movement of said plunger back out of said housing.

13. The assembly of claim 12 wherein said co-operating latching means includes a depressible button on said housing adapted to retain said first spring in a compressed condition and to release said first spring from its compressed condition when depressed.

* * * * *